(12) United States Patent
Ota et al.

(10) Patent No.: US 7,321,287 B2
(45) Date of Patent: Jan. 22, 2008

(54) GAS SENSOR

(75) Inventors: Nobuhiro Ota, Itami (JP); Jin-Joo Park, Itami (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 88 days.

(21) Appl. No.: 11/429,322

(22) Filed: May 8, 2006

(65) Prior Publication Data

US 2006/0255902 A1    Nov. 16, 2006

(30) Foreign Application Priority Data

May 10, 2005  (JP)  ............... 2005-137587
Feb. 22, 2006  (JP)  ............... 2006-045274

(51) Int. Cl.
*H01C 3/04* (2006.01)

(52) U.S. Cl. .................. 338/25; 338/28; 204/192 S; 204/406

(58) Field of Classification Search .......... 338/25, 338/28, 34, 35; 204/195 S, 294, 406, 425, 204/426
See application file for complete search history.

(56) References Cited

U.S. PATENT DOCUMENTS

| 4,049,524 | A | * | 9/1977 | Togawa et al. | ............ | 204/427 |
| 4,306,957 | A | | 12/1981 | Ishitani et al. | | |
| 4,455,214 | A | | 6/1984 | Isenberg | | |
| 4,595,485 | A | * | 6/1986 | Takahashi et al. | .......... | 204/406 |
| 6,420,262 | B1 | * | 7/2002 | Farrar | ........................ | 438/652 |
| 2003/0006875 | A1 | * | 1/2003 | Geissinger et al. | ........... | 338/25 |

FOREIGN PATENT DOCUMENTS

| EP | 0 678 740 A1 | 10/1995 |
| JP | 8-271476 A | 10/1996 |
| JP | 10-90220 A | 4/1998 |
| JP | 2885336 | 2/1999 |
| JP | 2000-62077 A | 2/2000 |
| WO | WO 94/27929 | 12/1994 |

OTHER PUBLICATIONS

Kogyo Kanetsu, "Industrial Heating," vol. 41, No. 6, pp. 31-36.
European Search Report issued in corresponding European Patent Application No. EP 06 25 2339, dated Sep. 12, 2006.

* cited by examiner

*Primary Examiner*—K. Richard Lee
(74) *Attorney, Agent, or Firm*—McDermott Will & Emery LLP

(57) ABSTRACT

According to one embodiment, the gas sensor includes a porous plate-like sintered body comprising trisilicon tetranitride needle crystals; two first catalyst metal thin films and one second catalyst metal thin film, formed on one surface of the plate-like sintered body in a non-contacted state with each other; oxygen ion-conductive solid electrolyte thin films formed on the respective surface; a surface layer thin film formed on the respective surfaces, so that a first measurement part, a second measurement part and a third measurement part are constituted; and a glass sealing layer comprising silicon oxide, formed on other surface of the porous plate-like sintered body, a surface other than the surface of the porous plate-like sintered body having the first catalyst metal thin film and the second catalyst metal thin film formed thereon, and a side of the first measurement part and the second measurement part.

2 Claims, 3 Drawing Sheets

GAS SENSOR

BACKGROUND OF THE INVENTION

1. Field of the Invention

The present invention relates to a gas sensor for measuring a content of nitrogen oxide and oxygen, contained in a combustion exhaust gas.

2. Description of the Background Art

As a gas sensor for measuring a content of nitrogen oxide and oxygen, contained in a combustion exhaust gas, a sensor is known, which has a structure constituted of a first chamber for pumping oxygen and a second chamber relating to measurement of nitrogen oxide, and which measures an oxygen concentration in the first chamber, and simultaneously reduces the oxygen concentration in a measurement gas up to about 10 ppm, decomposes by reduction the nitrogen oxide in the second chamber, detects the generated oxygen by pumping in the similar manner, and measures a concentration of a nitrogen oxide gas, as described in, for example, JP-A-10-90220, Japanese Patent 2,885,336, and Kogyo Kanetsu (Industrial Heating), vol. 41, No. 6, pp. 31-36. Those sensors are produced by bonding thin plates of yttrium oxide-added zirconium oxide (hereinafter referred to as "YSZ" for brevity) sintered body.

Further, a sensor is known, wherein a substrate comprises a YSZ film formed on a trisilicon tetranitride ($Si_3N_4$) (hereinafter referred to as "silicon nitride" for brevity) porous sintered body comprising needle crystals, as described in, for example, JP-A-2000-62077.

The sensor having such a structure achieves to shorten a temperature rising time due to lowering in measurement temperature and improvement in thermal shock resistance.

However, the sensors described in JP-A-10-90220, Japanese Patent 2,885,336, and Kogyo Kanetsu (Industrial Heating), vol. 41, No. 6, pp. 31-36 each use a thick plate material. As a result, heating at 700° C. or higher is required, and it takes 15 minutes or longer for temperature rising, and further, it takes 30 minutes or longer until a stable output is obtained. In addition, the structure of bonded sintered bodies generally has the problem that breakage may occur at bonded portions by repeating temperature rising and cooling.

The above-described conventional sensors each are constituted of two parts, a part for exhausting oxygen gas and a part for measuring NOx gas. Therefore, where exhaustion of oxygen gas in the pre-stage is not sufficient, or there is scattering in exhaustion, the residual oxygen leads to an error in measurement of NOx at the NOx measurement part, and the problem occurs in measurement accuracy of ppm order.

The sensor described in JP-A-2000-62077 involves gas diffusion from a thickness direction. Thus, function as a gas diffusion layer is not sufficient, and there is the problem that accuracy of quantification deteriorates.

SUMMARY OF THE INVENTION

The present invention has been made in view of the disadvantages in the prior art.

Accordingly, an object of the present invention is to provide a gas sensor that can shorten a rise time of a sensor, lower a heating temperature for preventing a joined portion of a sintered body from being broken, and improve accuracy of quantification.

According to one embodiment of the present invention, there is provided a gas sensor comprising:

a porous plate-like sintered body comprising trisilicon tetranitride needle crystals;

one first catalyst metal thin film comprising a first catalyst metal and one second catalyst metal thin film comprising a second crystal metal, formed on one surface of the plate-like sintered body in the order from an introduction side of a measurement gas in a state that the first catalyst metal thin film and the second catalyst metal thin film are non-contacted with each other;

oxygen ion-conductive solid electrolyte thin films formed on the respective surfaces of the first catalyst metal thin film and the second catalyst metal thin film;

a surface layer thin film comprising the first catalyst metal, formed on each surface of the respective ion-conductive solid electrolyte thin films in a state that the first catalyst metal thin film and the second catalyst metal thin film are non-contacted with each other, so that a first measurement part and a third measurement part are constituted; and a glass sealing layer comprising silicon oxide, formed on other surface of the porous plate-like sintered body, a surface other than the surface of the porous plate-like sintered body having the first catalyst metal thin film and the second catalyst metal thin film formed thereon, and a side of the first measurement part and the third measurement part.

According to another embodiment of the present invention, there is provided a gas sensor comprising:

a porous plate-like sintered body comprising trisilicon tetranitride needle crystals;

two first catalyst metal thin films each comprising a first catalyst metal and one second catalyst metal thin film comprising a second catalyst metal, formed on one surface of the plate-like sintered body in the order from an introduction side of a measurement gas in a state that the first catalyst metal thin films and the second catalyst metal thin film are non-contacted with each other;

oxygen ion-conductive solid electrolyte thin films formed on the respective surface of the two first catalyst metal thin films and the one second catalyst metal thin film;

a surface layer thin film comprising the first catalyst metal, formed on each surface of the respective ion-conductive solid electrolyte thin films in a state that the two first catalyst metal thin films and the second catalyst metal thin film are non-contacted with each other, so that a first measurement part, a second measurement part and a third measurement part are constituted; and a glass sealing layer comprising silicon oxide, formed on other surface of the porous plate-like sintered body, a surface other than the surface of the porous plate-like sintered body having the first catalyst metal thin film and the second catalyst metal thin film formed thereon, and a side of the first measurement part, the second measurement part and the third measurement part, an output of the second measurement part being added to an output of the first measurement part, and the difference in the output of the second measurement being subtracted from an output of the third measurement part.

The gas sensor according to the present invention uses the oxygen ion-conductive solid electrolyte thin film in the first measurement part, the third measurement part, and optionally, the second measurement part. This makes it possible to lower a heating temperature, and also measure a concentration of each of oxygen and nitrogen oxide contained in a combustion gas in a very short period of a rise time.

In the gas sensor of the present invention, the porous plate-like sintered body comprising trisilicon tetranitride needle crystals is used as a substrate, and the first measurement part, the third measurement part, and optionally, the second measurement part are formed on the substrate. As a result, those measurement parts get in the porous plate-like sintered body, thereby preventing peeling and the like between each measurement part and the porous needle-like sintered body as the substrate.

A glass sealing layer is provided on a given position. This prevents gas diffusion from the portion other than the first measurement part, the third measurement part, and optionally, the second measurement part. As a result, accuracy of quantification can be improved.

Further, by the above constitution, the sensor according to the present invention can stabilize repeated measurements, and can further greatly reduce consumption of electric power.

In addition, where the first measurement part, the second measurement part and the third measurement part are provided, there is the following advantage. Oxygen gas is exhausted at the first measurement part through the solid electrolyte thin film, but the oxygen gas remains in an amount of from 10 to several ten ppm. However, by measuring such a residual oxygen gas at the second measurement part, the accuracy of oxygen gas measurement at the first measurement part and NOx gas measurement at the third measurement part can be improved. In other words, the accuracy of NOx gas measurement can further be improved as compared with the embodiment that only the first measurement part and the third measurement part are provided.

DETAILED DESCRIPTION OF THE INVENTION

The present invention is described in detail below.

Figure 1:
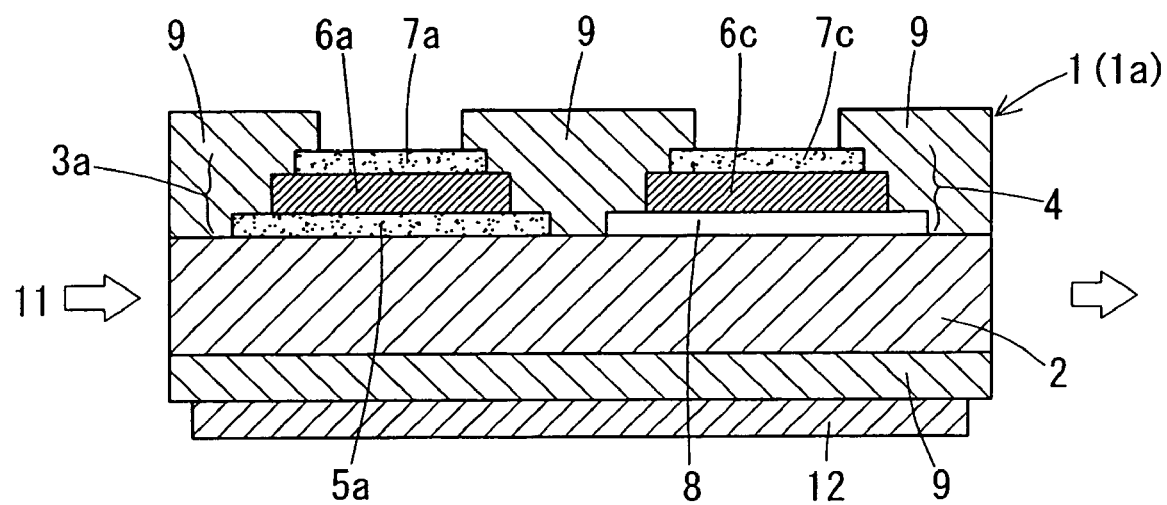
FIG. 1 is a cross-sectional view showing one embodiment of the gas sensor according to the present invention.
Figure 2:
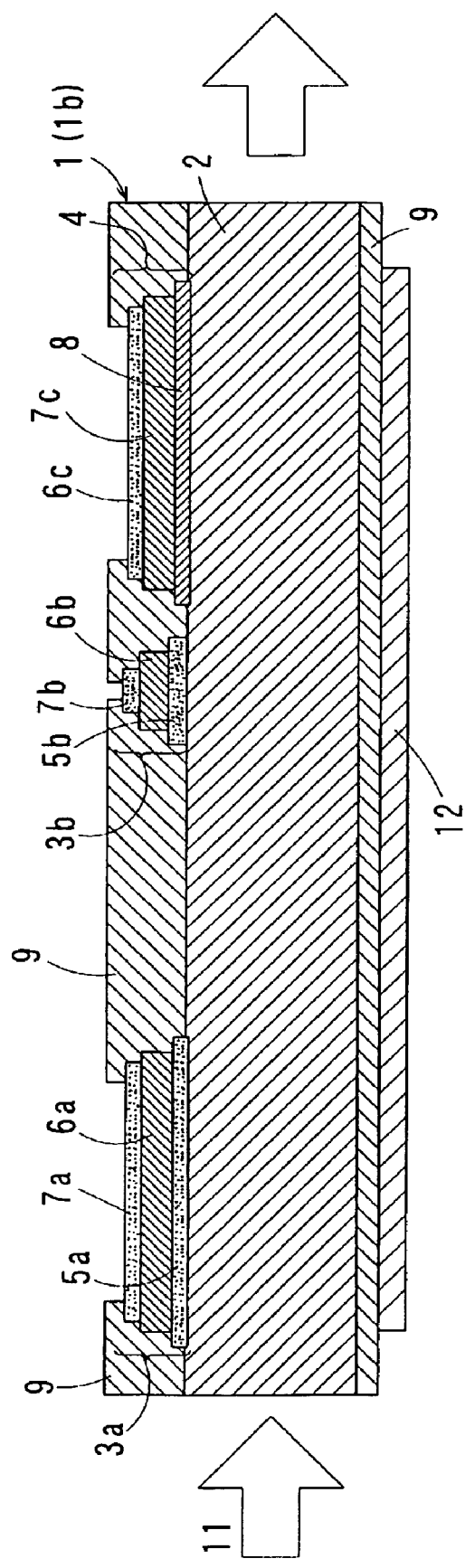
FIG. 2 is a cross-sectional view showing another embodiment of the gas sensor according to the present invention.

A sensor 1 according to the present invention comprises a first sensor 1a as shown in FIG. 1 or a second sensor 1b as shown in FIG. 2. As shown in FIG. 1, the first sensor 1a is a sensor comprising a given substrate 2, and given first measurement part 3a and third measurement part 4, formed on one surface of the substrate 2 in the order from an introduction side of a measurement gas 11 described hereinafter. As shown in FIG. 2, the sensor 1b is a sensor comprising a given substrate 2, and given first measurement part 3a, second measurement 3b and third measurement part 4, formed on one surface of the substrate 2 in the order from an introduction side of a measurement gas 11 described hereinafter. As is apparent from the comparison between the two constitutions, the difference between the first sensor 1a and the second sensor 1b is only the presence or absence of the second measurement part 3b. Specifically, the second measurement part 3b is formed in the sensor 1b. Therefore, the elements common to those two sensors (specifically, the elements constituting the first sensor 1a) are described together as the sensor 1, and the elements corresponding to only the second sensor 1b (specifically, the elements relating to the second measurement part 3b) are described separately or in a form of parentheses.

In the sensor 1, the substrate 2 comprises a porous plate-like sintered body. The porous plate-like sintered body is obtained by sintering trisilicon tetranitride ($Si_3N_4$) (hereafter referred to as "SiN" for simplicity) needle crystals, and has a structure that many SiN needle crystals are intertwined complicatedly.

The porous plate-like sintered body has a porosity of preferably from 30 to 80%. Where the porosity is less than 30%, a gas permeability of the sintered body tends to be insufficient. On the other hand, where the porosity exceeds 80%, such a sintered body has insufficient mechanical strength, and in addition thereto, the amount of first and second catalyst metals to supported on the sintered body becomes insufficient. As a result, there is the possibility that the resulting sensor does not exhibit the desired performance.

Pores in the porous plate-like sintered body have an average pore size of preferably from 0.01 to 50 μm, and more preferably from 0.05 to 1 μm. Where the average pore size is less than 0.01 μm, the gas permeability of such a sintered body tends to be insufficient. On the other hand, where the average pore size exceeds 50 μm, mechanical strength of such a sintered body tends to decrease.

The SiN needle crystals have an aspect ratio of preferably from 3 to 30. Where the aspect ratio is less than 3, mechanical strength of the crystal tends to be insufficient. On the other hand, the aspect ratio may exceed 30, but there is the possibility that it is difficult to produce such crystals. Therefore, the upper limit of the aspect ration is sufficient to be 30.

The SiN needle crystals have a length of minor axis of preferably from 0.05 to 10 μm, and more preferably from 0.1 to 1 μm. Where the length of minor axis is less than 0.05 μm, strength of the needle crystal becomes weak, and there is the tendency to lower the overall mechanical strength of the crystal. On the other hand, where the length of minor axis exceeds 10 μm, bonding points of mutual needle crystals decrease, and there is the tendency to cause the lowering of the overall mechanical strength of the crystals.

The porous plate-like sintered body has a thickness of preferably from 0.1 to 10 mm. Where the thickness is less than 0.1 mm, the mechanical strength of the sintered body decreases, and there is the possibility that such a porous plate-like sintered body cannot be put into a practical use. On the other hand, the length exceeds 10 mm, a gas is diffused or supplied exceeding the measurement ability, and there is the possibility of giving a hindrance to measurement accuracy.

The porous plate-like sintered body is preferably that a surface on which the catalyst metal film is formed is polished by buff polishing using alumina powder having a particle diameter of from 0.1 to 0.01 μm. By this polishing, a smooth surface is obtained, and a thin, dense solid electrolyte thin film can be formed. Where the particle diameter of alumina exceeds 0.1 μm, the surface of the sintered body becomes rough, and a sufficient polishing effect is not obtained. On the other hand, where the particle diameter of alumina is less than 0.01 μm, polishing efficiency deteriorates, which is not practical.

The porous plate-like sintered body can be produced by various methods. For example, the method described in PCT International Publication No. WO1994/27929 can be used. This method comprises molding a silicon nitride powder having a compound containing a rare earth element such as yttrium mixed therewith, according to the need, and then heat-treating the resulting molding at a temperature of from 1,500 to 2,100° C. under a nitrogen-containing atmosphere. By this method, needle crystals comprising β-$Si_3N_4$ can be precipitated, and thus a porous body having high porosity can be produced.

In the sensor 1, the first measurement part 3a comprises a laminate constituted by forming a first catalyst metal thin film 5a comprising a first catalyst metal on one surface of the substrate 2, forming an oxygen ion-conductive solid electrolyte thin film 6a on the surface of the first catalyst metal thin film 5a, and then forming a surface layer thin film 7a comprising the first catalyst metal on the surface of the oxygen ion-conductive solid electrolyte thin film 6a in a manner such that the surface layer thin film 7a and the first catalyst metal thin film 5a are non-contacted with each other.

In the sensor 1, the third measurement part 4 comprises a laminate constituted by forming a second catalyst metal thin film 8 comprising a second catalyst metal on one surface of the substrate 2, forming an oxygen ion-conductive solid electrolyte thin film 6c which is the same as the oxygen ion-conductive solid electrolyte thin film 6a on the surface of the second catalyst metal thin film 8, and then forming a surface layer thin film 7c which is the same as the surface layer thin film 7a on the surface of the oxygen ion-conductive solid electrolyte thin film 6c in a manner such that the surface layer thin film 7c and the second catalyst metal thin film 8 are non-contacted with each other.

In the second sensor 1b, the second measurement part 3b comprises a laminate constituted by forming a first catalyst metal thin film 5b comprising a first catalyst metal on one surface of the substrate 2, forming an oxygen ion-conductive solid electrolyte thin film 6b which is the same as the oxygen ion-conductive solid electrolyte thin film 6a on the surface of the first catalyst metal thin film 5b, and then forming a surface layer thin film 7b which is the same as the surface layer thin film 7a on the surface of the oxygen ion-conductive solid electrolyte thin film 6b in a manner such that the surface layer thin film 7b and the first catalyst metal thin film 5b are non-contacted with each other.

The first catalyst metal thin film 5a in the first sensor 1a, or the first catalyst metal thin films 5a and 5b in the second sensor 1b means a thin film comprising the above-described first catalyst metal. Examples of the first catalyst metal include platinum, nickel and a platinum-gold alloy. Of those, platinum is preferably used. The second catalyst metal thin film 8 in the sensor 1 means a thin film comprising the above-described second catalyst metal. Examples of the second catalyst metal include rhodium, ruthenium and a platinum-rhodium alloy. Of those, rhodium is preferably used.

Examples of the method of forming the first catalyst metal thin film 5a (or 5a and 5b) or the second catalyst metal thin film 8 on the substrate 2 include deposition by physical deposition, and the like. The first catalyst metal thin film 5a (or 5a and 5b) or the second catalyst metal thin film 8, formed on the substrate 2 by those methods is formed along needle crystals on the surface portion of the porous plate-like sintered body as the substrate 2, so that convexoconcaves (unevenness) are formed. Specifically, the first catalyst metal thin film 5a (or 5a and 5b) or the second catalyst metal thin film 8 is formed in the form of getting into the porous plate-like sintered body as the substrate 2. As a result, adhesion between the first catalyst metal thin film 5a (or 5a and 5b) or the second catalyst metal thin film 8 and the substrate 2 is improved, and this can prevent peeling between the first catalyst metal thin film 5a (or 5a and 5b) or the second catalyst metal thin film 8 and the substrate 2, breakage of those, and the like.

Examples of the physical deposition include vacuum deposition, sputtering, and ion plating. The vacuum deposition means a method of heat evaporating a metal or the like to be deposited in vacuum using a resistor or an electron gun, and condensing the same on the substrate, thereby forming a coating film. The sputtering means a method of colliding high energy ions with a target to fly away neutral target constituting atoms, accumulating the same on a counter substrate, and forming a coating film.

The ion plating means a method wherein part of evaporated particles in the vacuum deposition is ionized to increase movement energy, and thus improvement of film quality such as adhesion or denseness of a thin film formed can be made. Examples of the ion plating include polycathode thermoelectron irradiation method, high frequency excitation method, hollow cathode method, cluster ion beam method, activating reaction deposition method, and arc ion plating method.

The first catalyst metal thin film 5a (or 5a and 5b) or the second catalyst metal thin film 8 formed by the above methods are formed such that those are non-contacted with each other. By making those in a non-contacted state, the first measurement part 3a (or the first measurement part 3a and the second measurement part 3b) and the third measurement part 4 can be made non-contacted. By this structure, measurement at the first measurement part 3a, measurement at the third measurement part 4, and optionally, measurement at the second measurement part 3b can be conducted independently.

The oxygen ion-conductive solid electrolyte thin films 6a (or 6a and 6b) and 6c formed on the respective surface of the first catalyst metal thin film 5a (or 5a and 5b) and the second catalyst metal thin film 8 mean a thin film comprising a solid electrolyte having high oxygen ion conductivity. Examples of the solid electrolyte include zirconium oxide ($ZrO_2$)-based, cerium oxide ($CeO_2$)-based, and lanthanum gallate ($LaGaO_3$)-based solid electrolytes. Examples of the zirconium oxide-based solid electrolyte include solid solutions comprising zirconium oxide having added thereto yttrium oxide, gadolinium oxide, samarium oxide and the like. Examples of the cerium oxide-based solid electrolyte include solid solitions comprising cerium oxide having added thereto yttrium oxide, gadolinium oxide, samarium oxide and the like. Examples of the lanthanum gallate-based solid electrolyte include solid solutions comprising lanthanum gallate having added thereto strontium oxide, magnesium oxide and the like.

The oxygen ion-conductive solid electrolyte thin films 6a (or 6a and 6b) and 6c have weak mechanical strength, but have high ion conductivity and can be formed as a thin film. For this reason, the sensor according to the present invention works even at low temperature of about 400° C., can greatly decrease its size, and can shorten the time required for temperature rising and stable output within 1 minute.

Formation of the oxygen ion-conductive solid electrolyte thin films 6a (or 6a and 6b) and 6c on the surface of the first catalyst metal thin film 5a (or 5a and 5b) and the surface of the second catalyst metal thin film 8, respectively, can be conducted by the same physical deposition method as in the method of forming the first catalyst metal thin film 5a (or 5a and 5b) and the second catalyst metal thin film 8.

The surface layer thin films 7a and 7c in the first sensor 1a, and the surface layer thin films 7a, 7b and 7c in the second sensor 1b are thin films comprising the above-described first catalyst metal. This thin film can be formed using the same physical deposition method as in the method of forming the first catalyst metal thin film 5a.

The lower limit of thickness of the first catalyst metal thin film 5a (or 5a and 5b) and the second catalyst metal thin film 8 each is preferably 0.01 µm. Where the thickness is less than 0.01 µm, it is difficult to form a continuous thin film, and there is the tendency that electrons cannot be supplied. On the other hand, the upper limit of the thickness of the thin films each is preferably 0.5 µm, and more preferably 0.1 µm or less. The thickness exceeding 0.5 µm results in clogging voids in the substrate comprising the needle crystals, and there is the problem that diffusion of gas is limited. The thickness is more preferably in a range of from 0.03 to 0.07 µm, and particularly about 0.05 µm.

The lower limit of thickness of the oxygen ion-conductive solid electrolyte thin films 6a (or 6a and 6b) and 6c each is preferably 0.5 µm. Where the thickness is lower than 0.5 µm, pinholes generate too much in the oxygen ion-conductive solid electrolyte thin films, and gas diffusion from the pinholes is in a level which cannot be disregarded. As a result, there is the problem that an error of measurement data becomes large. On the other hand, the upper limit of thickness of the oxygen ion-conductive solid electrolyte thin films each is preferably 20 µm, and more preferably 10 µm. Where the thickness exceeds 20 µm, stress in the oxygen ion-conductive solid electrolyte thin film is too large, resulting in deterioration of thermal shock resistance of the thin film. Thus, there is the tendency that heat cycle life of the sensor decreases. The thickness is more preferably in a range of from 3 to 7 µm, and particularly about 5 µm.

A glass sealing layer 9 comprising silicon oxide as the main component is formed on other surface of the substrate 2, a surface other than the surface of the substrate having the first catalyst metal thin film 5a (or 5a and 5b) and the second catalyst metal thin film 8 formed thereon, and a side of the first measurement part 3a, the second measurement part (in the case of the second sensor 1b) and the third measurement part 4. By the formation of the glass sealing layer, the gas diffusion can be limited to only gas diffusion from the surface layer thin film 7a (or 7a and 7b) and 7c, and a diffusion rate-determining layer can be made complete. The glass comprising silicon oxide, used in the glass sealing layer 9 includes a borosilicate-based glass and the like.

Action of the sensor 1 (the first sensor 1a and the second sensor 1b) according to the present invention is described below.

In the sensor 1 according to the present invention, the first catalyst metal thin film 5a and the surface layer thin film 7a in the first measurement part 3a are provided with lead-in wires (not shown), respectively, and voltage is applied thereto. Similarly, in the case of the second sensor 1b, the first catalyst metal thin film 5b and the surface layer thin film 7b in the second measurement part 3b are provided with lead-in wires (not shown), respectively, and voltage is applied thereto.

Further, in the sensor 1 according to the present invention, the second catalyst metal thin film 8 and the surface layer thin film 7c in the third measurement part 4 are provided with lead-in wires (not shown), respectively, and voltage is applied thereto. When ions generated from a gas 11 flow into the first measurement part 3a, electric current generates. An inflow amount of oxygen can be measured from the electric current value, and as a result, an amount of oxygen in the gas 11 can be calculated.

The first catalyst metal thin film 5a in the first measurement part 3a (in the case of the second sensor, the first catalyst metal thin film 5a in the first measurement part 3a and the first catalyst metal thin film 5b in the second measurement part 3b) causes a reaction of converting nitrogen dioxide into nitrogen monoxide. However, further reaction does not occur, and generally, in the case of using a gas such as air, a reaction evolving oxygen does not occur. As a result, the amount of oxygen measured in the first measurement part 3a corresponds to the amount of oxygen contained in the gas 11.

On the other hand, the second catalyst metal thin film 8 in the third measurement part 4 causes a reaction of converting nitrogen monoxide into nitrogen and oxygen. As a result, the amount of oxygen measured in the third measurement part 4 is the sum of the amount of oxygen contained in the gas 11 and the amount of oxygen generated from nitrogen monoxide.

Therefore, the amount of oxygen generated from nitrogen monoxide can be calculated from the measurement data in the first measurement part 3a and the measurement data in the third measurement part 4. As a result, the amount of nitrogen monoxide contained in the gas 11 can be calculated.

However, there is the possibility that scattering causes in the measurement in the first measurement part 3a due to scattering of the initial oxygen concentration in the gas supplied to the sensor 1, or scattering causes in the amount of residual oxygen in the gas 11 to be sent to the third measurement part 4, and this gives an error to the measurement of NOx in the third measurement part 4.

In view of the above, accuracy of measurement in the first measurement part 3a and the third measurement part 4 can further be improved by measuring the amount of residual oxygen in the first measurement part 3a at the second measuring part 3b.

The representative measurement method of the sensor 1 is described. Specifically, Pt heater 12 is mounted on the bottom of the sensor 1, i.e., a surface opposite the surface having the first measurement 3a, the second measurement 3b and the third measurement part 4, by baking, and the sensor 1 is heated to a temperature of from 250 to 600° C., and preferably from 350 to 500° C., using the heater. This can cause reactions in the first measurement part 3a (in the case of the second sensor 1b, the first measurement part 3a and the second measurement part 3b), and the third measurement part 4, and also can improve oxygen conductivity of the oxygen ion-conductive solid electrolyte thin films 6a, 6b and 6c in the first measurement part 3a (in the case of the second sensor, the first measurement part 3a and the second measurement part 3b), and the third measurement part 4.

The gas 11 containing nitrogen oxide to be measured is poured from the edge of the substrate 2. Part of the gas 11 passes through the first measurement part 3a and is then discharged into the outside, and other part of the gas 11 passes through the second measurement part 3b and is then discharged into the outside.

In the first sensor 1a, the oxygen content in the gas 11 is calculated by passing the gas 11 through the first measurement part 3a as described above. Further, the sum of the amount of oxygen remaining in the gas 11 in a concentration of several 10 ppm or lower in the first measurement part 3a, and the amount of oxygen generated from nitrogen oxide is calculated by passing the gas 11 through the third measurement part 4 as described above. From those calculations, it is possible to calculate the amount of nitrogen oxide in the gas 11, which becomes a concentration of several hundred ppm.

In the second sensor 1b, the oxygen content in the gas 11 is calculated by passing the gas 11 through the first measurement part 3a as described above. The amount of oxygen remaining in the gas 11 is calculated by passing the gas 11 through the second measurement part 3b. Further, the sum of the oxygen content and the amount of oxygen generated from nitrogen oxide is calculated by passing the gas 11 through the third measurement part 4. Specifically, the amount of oxygen is calculated by adding an output of the second measurement part 3b to an output of the first measurement part 3a, and the amount of nitrogen oxide is calculated by subtracting the output of the second measurement part from an output of the third measurement part. From those calculations, it is possible to calculate the amount of nitrogen oxide in the gas 11. For this reason, the oxygen content in the gas 11 sent to the third measurement part 4 is measured in the second measurement part 3b, and this makes it possible to correct a measurement error of the amount of oxygen in the first measurement part 3a and also a measurement error of the amount of nitrogen oxide in the third measurement part 4. By this, measurement accuracy of nitrogen oxide can further be improved as compared with the case of the first sensor 1a having provided with only the first measurement part 3a and the third measurement part 4.

The present invention is described in more detail by reference to the following examples, but it should be understood that the invention is not construed as being limited thereto.

Production Method of Sensor:

The sensor 1a as shown in FIG. 1 and the sensor 1b as shown in FIG. 2 were produced according to the following methods.

Production of Substrate 2:

A trisilicon tetranitride sintered body was prepared according to the method described in PCT International Publication No. WO1994/27929. Specifically, a molding assistant was added to a silicon nitride powder comprising as the main component α-silicon nitride (α-$Si_3N_4$) having an average particle diameter of 0.3 μm (specific surface area: 11 $m^2$/g), and the resulting mixture was molded using a mold having a size of 100 mm×100 mm under a pressure of 20 kg/$cm^2$. The resulting molding was heat treated at 1,800° C. under an atmosphere pressure of 4 atm for 2 hours to obtain a trisilicon tetranitride sintered body. The sintered body obtained had a thickness of 0.5 mm, an average pore size of 0.1 μm and a porosity of 40%.

The trisilicon tetranitride sintered body thus obtained was cut into a piece of 5 mm×10 mm, and the cut piece was used as a substrate 2.

Formation of First Catalyst Metal Thin Film 5a (In the Case of Second Sensor 1b, First Catalyst Thin Films 5a and 5b):

The substrate 2 obtained above was fixed to a substrate holder having been subjected to a groove processing in the same shape of the substrate, and a mask having one window of 4 mm square (in the case of the second sensor 1b, two windows) was then fixed to one surface of the substrate 2. Pt metal film was formed by a sputter film-forming method on the window portion so as to cover a surface of needle crystals constituting the substrate 2 in a thickness of 0.05 μm without embedding pores. Thus, a first catalyst metal thin film 5a (in the case of the second sensor 1b, first catalyst metal thin films 5a and 5b which are non-contacted with each other) was formed.

Formation of Second Catalyst Metal Thin Film 8:

While fixing the substrate 2 having formed thereon the first catalyst metal thin film 5a (in the case of the second sensor 1b, the first catalyst metal thin films 5a and 5b) to the substrate holder having been subjected to a groove processing in the same shape of the substrate 2, the mask used to form the Pt metal film was removed, and a fresh mask having a window having a size of 4 mm square was fixed to a position neighboring the first catalyst metal thin film 5a (in the case of the second sensor 1b, a position neighboring the first catalyst metal thin film 5b, and an opposite side of the first catalyst metal thin film 5a) without overlapping with the first catalyst metal thin film 5a (in the case of the second sensor 1b, the first catalyst metal thin film 5b). Rh metal film was formed on the window portion by a sputter film-forming method so as to cover a surface of needle crystals constituting the sintered body in a thickness of 0.05 μm without embedding pores. Thus, a second catalyst metal thin film 8 was formed.

Formation of Oxygen Ion-conductive Solid Electrolyte Thin Film 6a (In the Case of Second Sensor 1b, First Catalyst Metal Thin Films 6a and 6b) and 6c:

While fixing the substrate 2 used to form the second catalyst metal thin film 8 to the substrate holder having been subjected to a groove processing in the same shape of the substrate, a fresh mask which had formed the Rh metal film was removed, and a fresh mask for the formation of a solid electrolyte thin film having two windows each having 3 mm square opening was fixed such that the two openings match on the respective surfaces of the Pt metal film-formed portion (the first catalyst metal thin film 5a (in the case of the second sensor 1b, the first catalyst metal thin films 5a and 5b) and the Rh metal-formed portion (the second catalyst metal thin film 8).

The resulting assembly including the substrate holder was set in a film-formation apparatus by KrF excimer laser abrasion method.

Separately, a $CeO_2$ powder having 5 mol % of $Gd_2O_3$ powder mixed therewith was placed in a mold, and molded by an oil pressure press to obtain a target having a diameter of 20 mm and a thickness of 5 mm. This target was set to a predetermined position in the film-formation apparatus.

Excimer laser having an output of 600 mJ/pulse and a repeating rate of 5 Hz was concentrated with a convex lens, and the target was irradiated with such a concentrated excimer laser. The degree of vacuum in the film formation was an oxygen atmosphere of $1.33\times10^{-2}$ Pa. Temperature of the substrate was room temperature at the initial stage of film formation, and was controlled so as to gradually elevate with the progress of film formation. The final substrate temperature was 700° C., and the temperature was risen to 700° C. over the initial 1 hour in the film formation time. After reaching the temperature to 700° C., the temperature was maintained constant. The overall film formation time of a solid electrolyte thin film was 3 hours. The solid electrolyte thin film was formed on a quartz substrate provided for measurement of film thickness, and the film thickness of the thin film was measured with a stylus profiler. As a result, it was found that the thickness is 5 μm. Thus, the oxygen ion-conductive solid electrolyte thin films 6a (in the case of the second sensor 1b, the oxygen ion-conductive solid electrolyte thin films 6a and 6b) and 6c were formed.

Formation of Surface Layer Thin Films 7a (In the Case of Second Sensor 1b, Surface Layer Thin Films 7a and 7b) and 7c:

While fixing the substrate 2 having formed thereon the oxygen ion-conductive solid electrolyte thin films 6a (in the case of the second sensor 1b, the oxygen ion-conductive solid electrolyte thin films 6a and 6b) and 6c to the substrate holder having been subjected to a groove processing in the same shape of the substrate, the mask used to form the solid electrolyte thin film was removed, and a fresh mask having two (or three) windows each having 2.5 mm square opening was fixed such that the two (three) openings match on the respective surfaces of the solid electrolyte thin films 6a (in the case of the second sensor 1b, the oxygen ion-conductive solid electrolyte thin films 6a and 6b) and 6c. Pt metal film was formed on the surfaces of the window portions in a thickness of 0.01 μm by a sputter film-forming method. Thus, surface layer thin films 7a (in the case of second sensor 1b, surface layer thin films 7a and 7b) and 7c were formed.

Formation of Glass Sealing Layer 9:

A borosilicate glass was welded on the entire surface of the back of the substrate 2 having formed thereon the surface layer thin films 7a (in the case of second sensor 1b, surface layer thin films 7a and 7b) and 7c, two side portions having long side of the substrate 2, and a portion on the surface of the substrate 2 having formed thereon the surface layer thin films 7a (in the case of second sensor 1b, surface layer thin films 7a and 7b) and 7c, but the surface not having the surface layer thin films 7a (in the case of second sensor 1b, surface layer thin films 7a and 7b) and 7c formed thereon, thereby forming a sealing layer 9. Thus, a gas sensor 1 having a structure as shown in FIG. 1 was produced.

EXAMPLE

A gas 11 each having various nitrogen dioxide concentrations of from 0 to 1,000 ppm was prepared by adding nitrogen dioxide gas to a mixed gas having 21 vol % of oxygen, 79 vol % of nitrogen and a relative humidity at room temperature of 30%. Using the gas 11, sensor outputs of the first sensor 1a and the second sensor 1b were measured.

Specifically, the first sensor 1a and the second sensor 1b were placed in a measurement vessel, and a probe was contacted with both electrodes. Further, the sensors were set in the vessel in a manner such that the portion of the first catalyst metal thin film 5a faces the upstream side of the measurement gas.

Figure 3:
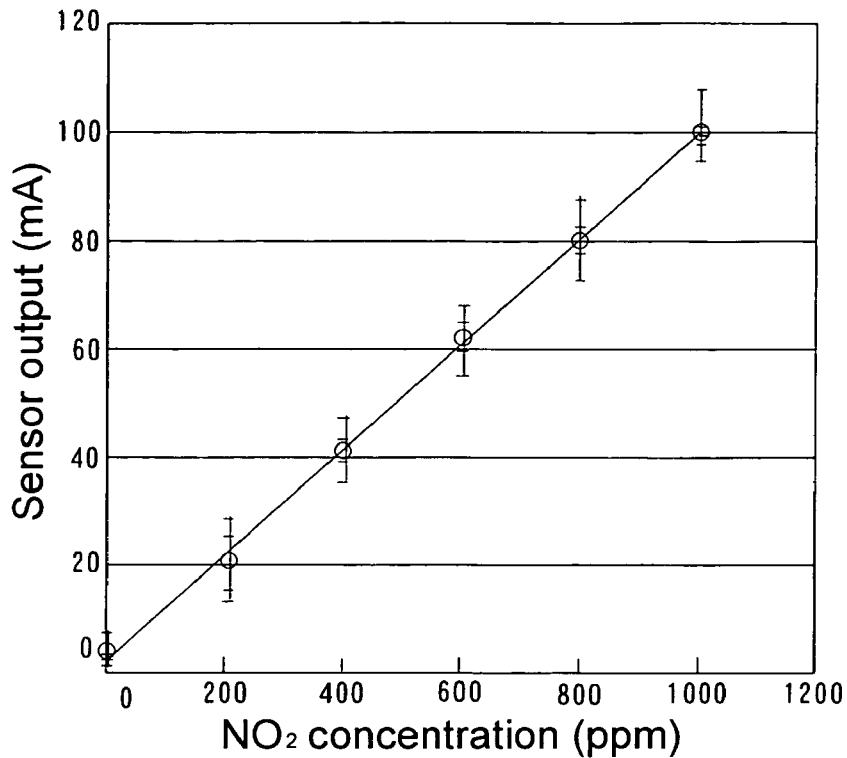
FIG. 3 is a graph showing the relationship between nitrogen dioxide concentration (ppm) and current output (mA) in the case of using the sensor (first sensor 1a) shown in FIG. 1 in the Example.
Figure 4:
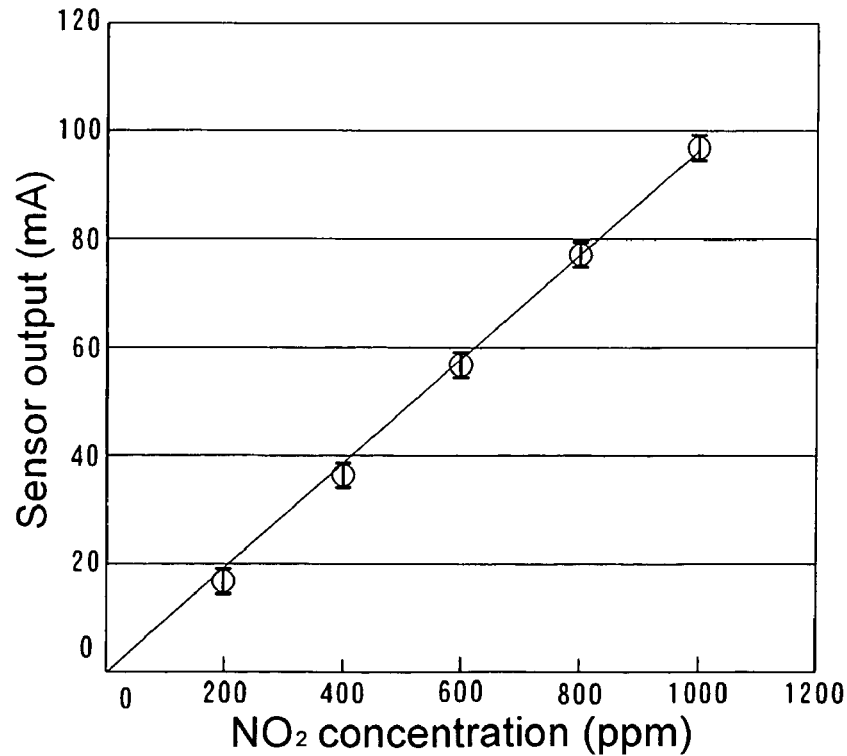
FIG. 4 is a graph showing the relationship between nitrogen dioxide concentration (ppm) and current output (mA) in the case of using the sensor (second sensor 1b) shown in FIG. 2 in the Example.

Temperature of the measurement portion was risen to 400° C. using Pt heater 12 mounted by baking on the glass sealing layer 9. Direct current voltage of 10 mV was applied, and its current output was measured. The results obtained using the first sensor 1a are shown in FIG. 3, and the results obtained using the second sensor 1b are shown in FIG. 4. Each output varied from 0 to 100 mA, and good linear output in proportion to the nitrogen oxide concentration could be obtained. Further, the measurement was not influenced by 21% oxygen concentration, and drifting and the like did not occur. Thus, stable measurement could be conducted. However, standard deviation of scattering in output data of the first sensor 1a was a wide width of about 6.4, whereas standard deviation of scattering in output data of the second sensor 1b was stable as about 1.5.

What is claimed is:

1. A gas sensor comprising:
   a porous plate-like sintered body comprising trisilicon tetranitride needle crystals;
   one first catalyst metal thin film comprising a first catalyst metal and one second catalyst metal thin film comprising a second crystal metal, formed on one surface of the porous plate-like sintered body in the order from an introduction side of a measurement gas in a state that the first catalyst metal thin film and the second catalyst metal thin film are non-contacted with each other;
   oxygen ion-conductive solid electrolyte thin films formed on the respective surface of the first catalyst metal thin film and the second catalyst metal thin film;
   a surface layer thin film comprising the first catalyst metal, formed on each surface of the respective ion-conductive solid electrolyte thin films in a state that the first catalyst metal thin film and the second catalyst metal thin film are non-contacted with each other, so that a first measurement part and a third measurement part are constituted; and
   a glass sealing layer comprising silicon oxide, formed on other surface of the porous plate-like sintered body, a surface other than the surface of the porous plate-like sintered body having the first catalyst metal thin film and the second catalyst metal thin film formed thereon, and a side of the first measurement part and the third measurement part.

2. A gas sensor comprising:
   a porous plate-like sintered body comprising trisilicon tetranitride needle crystals;
   two first catalyst metal thin films each comprising a first catalyst metal and one second catalyst metal thin film comprising a second catalyst metal, formed on one surface of the plate-like sintered body in the order from an introduction side of a measurement gas in a state that the first catalyst metal thin films and the second catalyst metal thin film are non-contacted with each other;
   oxygen ion-conductive solid electrolyte thin films formed on the respective surface of the two first catalyst metal thin films and the one second catalyst metal thin film;
   a surface layer thin film comprising the first catalyst metal, formed on each surface of the respective ion-conductive solid electrolyte thin films in a state that the two first catalyst metal thin films and the second catalyst metal thin film are non-contacted with each other, so that a first measurement part, a second measurement part and a third measurement part are constituted; and
   a glass sealing layer comprising silicon oxide, formed on other surface of the porous plate-like sintered body, a surface other than the surface of the porous plate-like sintered body having the first catalyst metal thin film and the second catalyst metal thin film formed thereon, and a side of the first measurement part, the second measurement part and the third measurement part,
   an output of the second measurement part being added to an output of the first measurement part, and the difference in the output of the second measurement being subtracted from an output of the third measurement part.

* * * * *